(12) United States Patent
Carmody et al.

(10) Patent No.: US 9,421,354 B2
(45) Date of Patent: Aug. 23, 2016

(54) CHECK VALVE WITH INTEGRATED FILTER

(71) Applicant: ILLINOIS TOOL WORKS INC., Glenview (IL)

(72) Inventors: Colm M. Carmody, Kerry (IE); Gerard G. Henn, Limerick (IE)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 14/758,255

(22) PCT Filed: Dec. 30, 2013

(86) PCT No.: PCT/US2013/078342
§ 371 (c)(1),
(2) Date: Jun. 29, 2015

(87) PCT Pub. No.: WO2014/107436
PCT Pub. Date: Jul. 10, 2014

(65) Prior Publication Data
US 2015/0352349 A1    Dec. 10, 2015

Related U.S. Application Data

(60) Provisional application No. 61/748,236, filed on Jan. 2, 2013.

(51) Int. Cl.
*F16K 15/14* (2006.01)
*A61M 39/22* (2006.01)
*A61M 5/165* (2006.01)
*A61M 39/24* (2006.01)

(52) U.S. Cl.
CPC ............... *A61M 39/22* (2013.01); *A61M 5/165* (2013.01); *A61M 39/24* (2013.01); *F16K 15/145* (2013.01); *A61M 2005/1657* (2013.01); *A61M 2039/2406* (2013.01); *A61M 2039/246* (2013.01); *A61M 2039/2433* (2013.01); *A61M 2205/75* (2013.01); *Y10T 137/794* (2015.04)

(58) Field of Classification Search
CPC ..... A61M 39/22; A61M 39/24; A61M 5/165; A61M 2005/1657; A61M 2039/2406; A61M 2039/2433; A61M 2039/246; A61M 2205/75; F16K 15/145; Y10T 137/794
See application file for complete search history.

(56) References Cited

U.S. PATENT DOCUMENTS

| 4,141,379 A | 2/1979 | Manske |
| 4,765,372 A | 8/1988 | Beecher |
| 5,195,986 A | 3/1993 | Kamen |

(Continued)

FOREIGN PATENT DOCUMENTS

| EP | 0129410 A2 | 12/1984 |
| EP | 2679273 A1 | 1/2014 |

(Continued)

OTHER PUBLICATIONS

ISR and WO for PCT/US2013/078342 mailed Apr. 3, 2014.

*Primary Examiner* — Jessica Cahill (57) ABSTRACT

A check valve suitable for use with IV sets and the like provides an upstream filter preventing contamination from affecting the sealing of the check valve membrane. The filter may employ filter media that is integrally bonded to the housing of the filter providing simple and robust construction.

13 Claims, 7 Drawing Sheets

(56) References Cited

U.S. PATENT DOCUMENTS

| | | | |
|---|---|---|---|
| 5,617,897 A | 4/1997 | Myers | |
| 7,997,293 B2 | 8/2011 | Ruschke | |
| 8,251,099 B2 | 8/2012 | Carmody et al. | |
| 2007/0163664 A1* | 7/2007 | Mijers | F16K 15/144 137/859 |
| 2007/0219535 A1 | 9/2007 | Phung et al. | |
| 2012/0004623 A1 | 1/2012 | Tumminaro et al. | |
| 2014/0005612 A1 | 1/2014 | Guala | |
| 2014/0299212 A1 | 10/2014 | Colm et al. | |

FOREIGN PATENT DOCUMENTS

| | | |
|---|---|---|
| FR | 2391405 A1 | 12/1978 |
| WO | 2010107597 A1 | 9/2010 |

\* cited by examiner

CHECK VALVE WITH INTEGRATED FILTER

CROSS-REFERENCE TO RELATED APPLICATIONS

This application is a National Phase of International Application No. PCT/US2013/078342 filed Dec. 30, 2013 and claims the benefit of U.S. application 61/748,236 filed on Jan. 2, 2013 and hereby incorporated by reference.

FIELD OF THE INVENTION

The present invention relates generally to one-way check valves and, more particularly, to one-way check valves used in medical fluid delivery systems; and, still more particularly, to contaminant screens and particulate isolating features to protect check valve performance in intravenous (IV) administration sets.

BACKGROUND OF THE INVENTION

It is known to provide intravenous (IV) drug and fluid delivery systems that include a primary line connected to a bag of saline or other fluids, and a branch or auxiliary line connectable to supplies of drugs or other treatment fluids. The branch line and main line are connected at a Y-connector. A check valve is provided in the main line to prevent backflow of the secondary fluid into the main fluid bag. When a drug is dispensed, the backflow pressure on the check valve closes the valve to prevent backflow of the drug into the saline or other non-drug bag. When a drug or other fluid is not dispensed from the auxiliary line, saline flows freely through the check valve.

A known check valve for this purpose is taught by U.S. Pat. No. 4,765,372 hereby incorporated by reference. The valve disclosed therein includes a housing, a biasable diaphragm within the housing and a valve seat carried by the housing against which the diaphragm is urgeable. The housing has a fluid inlet and a fluid outlet. The diaphragm is preferably disposed transverse to a preselected direction of fluid flow through the housing for controlling fluid flow therethrough. The diaphragm can be urged against the seat for preventing fluid from flowing contrary to the preselected direction of flow. The housing engages opposite sides of the diaphragm so that areas of the diaphragm can be moved away from and toward the valve seat without the diaphragm being displaced from its operative position within the valve.

While valves of the type described have worked successfully, contaminants in the system can interfere with proper operation. If a contaminant particle embeds itself in the diaphragm or seal surface, a proper seal may not be provided. The particle may prop open the diaphragm, in which case a drug dispensed from the secondary path may backflow through the check valve, thereby preventing the patient from receiving the proper drug dosage concentration or timely delivery of the drug.

Contaminants can be created during the manufacture and assembly of IV sets. Particles from many sources can migrate and be trapped in the IV set, and later be carried by fluids into the check valve. The sources of contaminant particles include and are byproducts of handling, processing and migration of other materials that work their way into the IV set system. For example, it is known to cut tubes and assemble bag spike components to enable attachment to associated devices. Cutting or puncturing the tube can generate tubing debris that can compromise the sealing function if the particles migrate to the check valve. Other particles from the environment also can be trapped in the IV set and be carried to the check valve.

PCT patent application WO 2010/107597, hereby incorporated by reference and assigned to the assignee of the present invention, describes a check valve having an integrated screen to trap contaminant particles away from a sealing area of the check valve.

SUMMARY OF THE INVENTION

The present invention provides improved methods of integrating upstream filters into check valve assemblies in which the filter medium is attached directly to the check valve housing element that provides the entrance port and/or valve seat. This close integration reduces assembly costs and provides a robust structure which prevents contaminants from interfering with sealing of the check valve.

Specifically, the invention provides a combination check valve and filter having a housing formed of first and second unitary molded thermoplastic elements joined to provide a cavity therebetween and providing fluid communication between an opposed entrance port formed in the first unitary molded thermoplastic element and an exit port formed in the second unitary molded thermoplastic element. A valve seat is attached to a cavity wall formed by the first unitary molded thermoplastic element and a flexible diaphragm responsive to fluid flow through the cavity is positioned adjacent to the valve seat to seal against the valve seat with fluid flow from the exit port to the entrance port and to unseal away from the valve seat with fluid flow from the entrance port to the exit port. Filter medium disposed in the housing between the entrance port and the valve seat and the filter medium is integrally bonded at its periphery to the first unitary molded thermoplastic element.

It is thus a feature of at least one embodiment of the invention to substantially reduce the number of parts and hence the cost of producing a combination filter check valve that can reduce check valve failure.

The entrance port may provide a counter-bore presenting a radial ledge facing away from the cavity and wherein the periphery of the filter medium abuts and is bonded to the ledge.

It is thus a feature of at least one embodiment of the invention to provide a simple and mechanically robust method of attachment of flexible filter media. It is a further feature of this embodiment to provide for post-assembly insertion of the filter after the housing components are joined.

The valve seat may extend about an opening of the entrance port into the cavity and, in an alternative embodiment, the periphery of the filter medium may cover the opening and be bonded to a cavity wall within the valve seat.

It is thus a feature of at least one embodiment of the invention to provide an integrated filter that adapts well to punch and molding assembly techniques or insert molding where the filter media is bonded by embedding its periphery in the molten plastic of the housing.

The filter medium may abut the flexible diaphragm when the flexible diaphragm seals against the valve seat to support the flexible diaphragm.

It is thus a feature of at least one embodiment of the invention to provide mechanical support of the flexible diaphragm against high-back pressures particularly important for edge supported diaphragms that rely on a stretching of the diaphragm material for compliance.

The filter medium may be a woven or nonwoven flexible fabric.

It is thus a feature of at least one embodiment of the invention to provide a readily assembled filter system that works with a variety of filter medium.

The filter medium may be bonded by embedding material of the filter within the thermoplastic of the first unitary molded thermoplastic element.

It is thus a feature of at least one embodiment of the invention to permit an assembly technique with high mechanical strength and short assembly time.

In some embodiments the filter medium may be a perforated thermoplastic element integrally molded as part of the first unitary molded thermoplastic element.

It is thus a feature of at least one embodiment of the invention to fully integrate the filter with the housing components to eliminate all assembly steps with respect to the filter.

The perforated thermoplastic element may provide a grid of a set of crossing rectilinear elements, the elements of each set crossing to abut at regular intersections.

It is thus a feature of at least one embodiment of the invention to provide a filter architecture well adapted to simple injection mold cavities.

The entrance port and exit port may be aligned along a central axis and first and second unitary molded thermoplastic elements may provide flanges extending radially from the axis about ends of the entrance port and exit port, the flanges joined at their peripheries to create the cavity.

It is thus a feature of at least one embodiment of the invention to provide a simple housing structure to permit low-cost manufacture of the combined filter and check valve.

The flanges may provide axially extending features that capture a periphery of the flexible diaphragm therebetween so that the entire periphery of the flexible diaphragm is held substantially stationary when the flexible diaphragm seals against the valve seat and unseals away from the valve seat.

It is thus a feature of at least one embodiment of the invention to provide a low backflow check valve using a peripherally supported diaphragm.

The valve seat may be integrally molded with the first unitary thermoplastic element or in an alternative embodiment the valve seat may be a third unitary molded thermoplastic element positioned between the first and second unitary molded thermoplastic elements retained thereby when the first and second unitary molded thermoplastic elements are joined thereby. In this latter case, the third unitary molded thermoplastic element may provide a central aperture having a first opening surrounded by the valve seat on a first side of the third unitary molded thermoplastic element facing the cavity and having a second opening on a second opposite side of the third unitary molded thermoplastic element. In this latter embodiment, the periphery of the filter medium may abut and be bonded to the second opposite side of the third unitary molded thermoplastic element about the second opening.

It is thus a feature of at least one embodiment of the invention to provide an additional housing component to form a secondary cavity for holding a filter element allowing increased filtration area without compromise of the valve action (for example by requiring enlargement of the valve seat such as might promote additional leakage).

The third unitary molded thermoplastic element may provide a filter medium that is a perforated thermoplastic element integrally molded as part of the third unitary molded thermoplastic element.

It is thus a feature of at least one embodiment of the invention to permit different molding techniques to be used on the housing and the filter medium to provide greater flexibility in creating small aperture filter media.

Other features and advantages of the invention will become apparent to those skilled in the art upon review of the following detailed description, claims and drawings in which like numerals are used to designate like features.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF THE PREFERRED EMBODIMENTS

Figure 1:
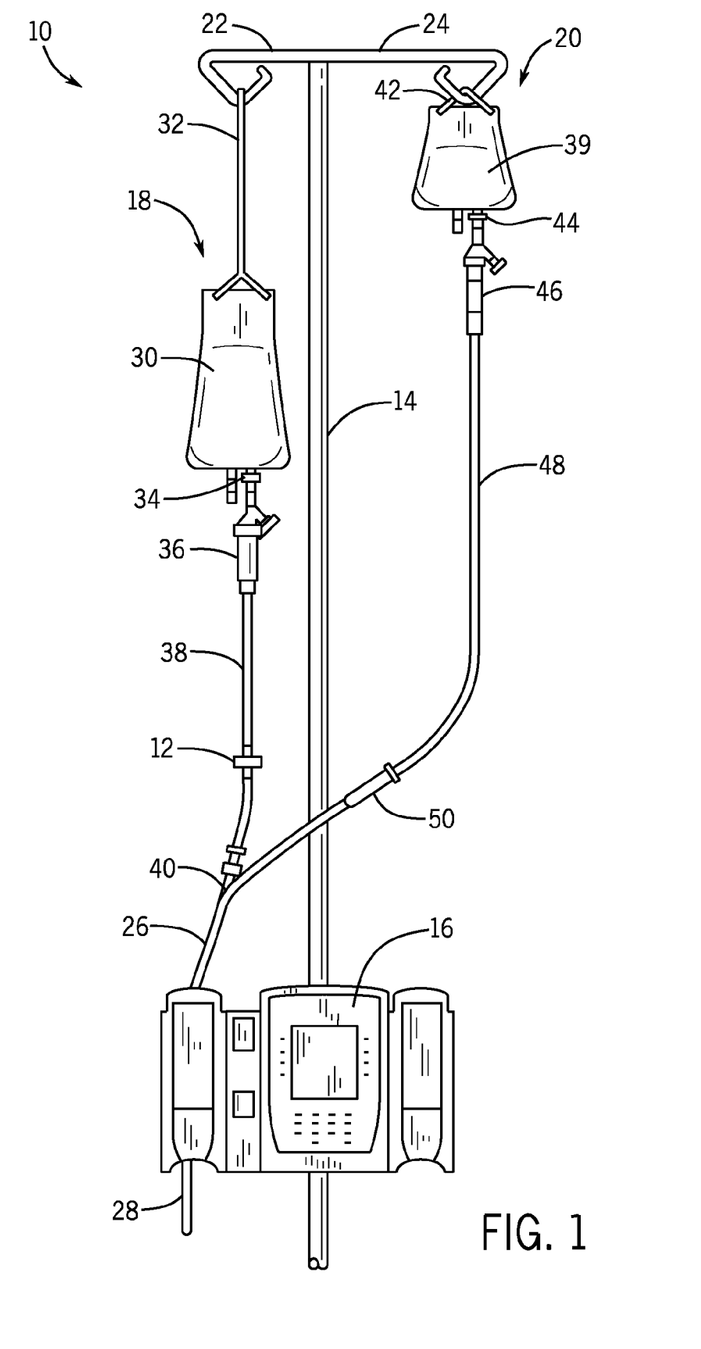
FIG. 1 is a fragmentary perspective view of an IV set having a filter/check valve of the present invention therein.

Referring now to FIG. 1, an IV set system 10 is shown and includes an IV check valve 12 therein. IV set system 10 includes an IV standard or pole 14 carrying an IV pump 16 thereon for administering fluid flow from a main fluid subsystem 18 and a branch or auxiliary fluid subsystem 20. IV standard or pole 14 includes first and second arms 22, 24 from which main fluid subsystem 18 and auxiliary fluid subsystem 20 are suspended. IV pump 16 receives fluid from main fluid subsystem 18 and branch or auxiliary fluid subsystem 20 via a supply line 26 and controls and dispenses the fluids therefrom to the patient via a patient IV line 28.

Main fluid subsystem 18 includes a main fluid source such as a fluid bag 30 which may include or contain saline solution or other fluid to be administered to the patient. Fluid bag 30 is suspended from arm 22 by a tether or strap 32. An outlet feature 34 from fluid bag 30 is connected to a drip chamber 36. A fluid line 38 carries flow from drip chamber 36 to a Y-connector 40. Check valve 12 is disposed in fluid line 38 upstream from Y-connector 40 and enables flow from fluid bag 30 to IV pump 16 while preventing backflow of fluid from an auxiliary fluid subsystem 20 toward fluid bag 30.

Branch or auxiliary fluid subsystem 20 includes an auxiliary fluid source such as a fluid bag 39 which may contain drugs or other fluid to be supplied to the patient for treatment. Fluid bag 39 is suspended from arm 24 by a tether or strap 42. An outlet feature 44 from fluid bag 39 is connected to a drip chamber 46. An auxiliary fluid line 48 carries flow from drip chamber 46 to Y-connector 40. A flow regulator 50 can be used in fluid line 48 to control the rate of flow from the fluid bag 39 to IV pump 16.

It should be understood that, apart from check valve 12 to be described in further detail hereinafter, the exemplary IV set system 10 components shown and described are merely exemplary in nature, and check valve 12 can be used in other types of IV systems as well as in fluid flow systems of other types, for other purposes.

Figure 2:
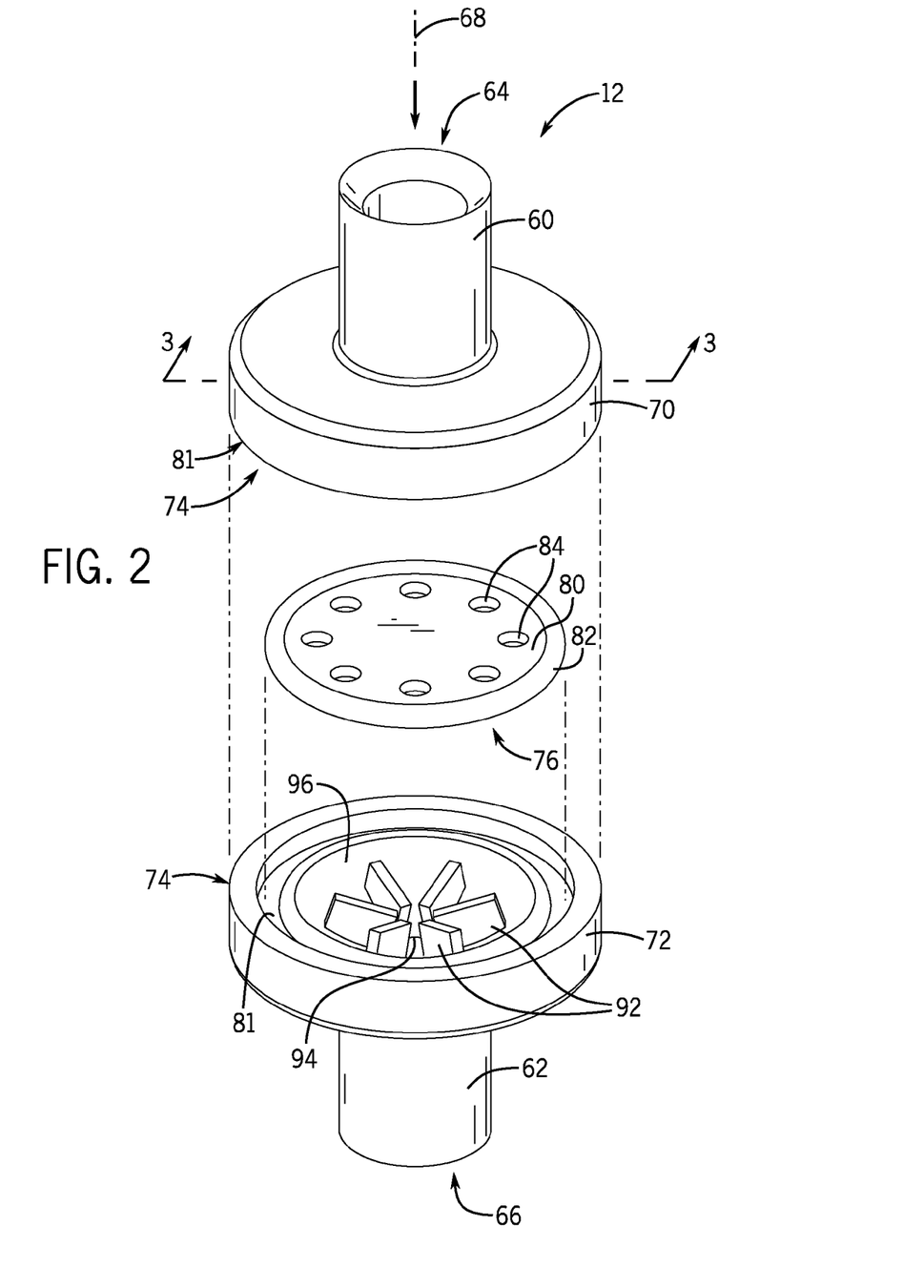
FIG. 2 is an exploded perspective diagram of a first embodiment of the invention showing upper and lower housing components as may contain a flexible diaphragm providing a check valve function.

Referring now to FIG. 2, the check valve 12 may provide for an entrance housing section 60 and an exit housing section 62 each having bores 64 and 66 respectively extending along a common axis 68. The bores 64 and 66 may receive upper and lower ends of the fluid line 38, discussed with respect to FIG. 1, according to attachment methods well known in the art.

Opposed ends of the bores 64 and 66 may open through flanges 70 and 72 respectively on the entrance housing section 60 and exit housing section 62, the flanges 70 and 72 extending radially about the axis 68. The opposing flanges 70 and 72 may join together at their peripheries 74 to define a liquid-tight cavity 76 being part of a continuous passage from the bore 64 of entrance housing section 60 to the bore 66 of exit housing section 62.

Each of the entrance housing section 60 and exit housing section 62 may be unitary molded thermoplastic components, for example, molded with a single injection of thermoplastic into a mold cavity. The thermoplastic material may be any of various synthetic materials such as polyethylene, polypropylene or the like providing medical grade biocompatible materials.

A circular elastomeric membrane 80 may have an enlarged rim 82 that may be captured in opposed channels 81 extending about the peripheries 74 of the flanges 70 and 72. When the rim 82 is captured in the channels 81, a center section of the elastomeric membrane 80 may flex toward the entrance housing section 60 or toward the exit housing section 62 with the flow of fluid through the check valve 12. A set of peripheral openings 84 may be provided in-between the rim 82 and the center of the elastomeric membrane 80 to permit this flow. Elastomeric membrane 80 is a flexible and resilient material such as a synthetic rubber impervious to fluid.

Figures 3, 4:
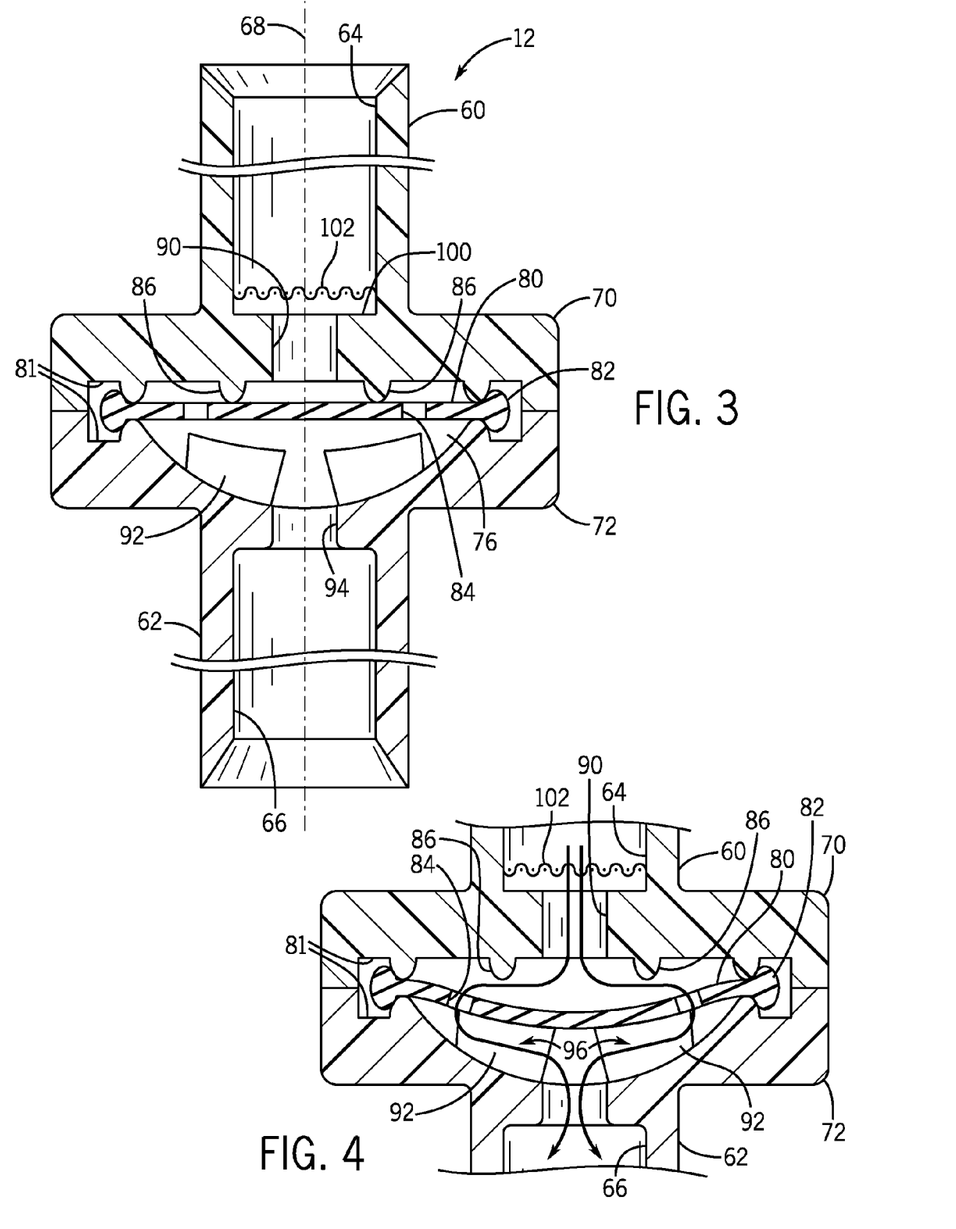
FIG. 3 is a cross-sectional view of the first embodiment of the invention taken along line 3-3 with the flexible diaphragm in a sealed position against backflow.
FIG. 4 is a fragmentary portion of FIG. 3 with the flexible diaphragm in the open position allowing forward flow.

Referring now to FIG. 3, when fluid flow is backward toward entrance housing section 60, the elastomeric membrane 80 is pulled against the rim of an annular valve seat 86 surrounding an opening 90 of the bore 64 and extending into the cavity 76. The annular valve seat 86 is positioned inside of the peripheral openings 84 and thus when the annular valve seat 86 contacts the elastomeric membrane 80 it blocks the only passageway between the bore 64 and cavity 76, sealing that check valve 12 against flow to essentially block backflow.

Referring to FIG. 2, conversely when fluid flow is forward and downward toward exit housing section 62, the elastomeric membrane 80 is pulled against radial ribs 92 blocking further distention of the elastomeric membrane 80 but allowing flow through the peripheral openings 84 and channels 96 in the exit housing section 62 through opening 94 leading to the exit bore 66.

In the embodiment of FIGS. 3 and 4, bore 64 is a counter bore providing an axially radial and upwardly facing ledge 100 formed by a reduction in diameter of the bore 64 as it enters cavity 76 through opening 90. Filter medium 102, for example, in the form of a disk having a diameter equal to the diameter of the large portion of the bore 64 may be bonded at its periphery to the ledge 100 to cover the opening 90. The bonding system may employ ultrasonic welding, heat sealing, gluing or other attachment methods. In one embodiment, the bonding may embed the material of the filter medium 102 within the thermoplastic of the entrance housing section 60, for example, by insert molding or by partially melting the thermoplastic material of the entrance housing section 60 and/or the filter medium 102.

Figure 5:
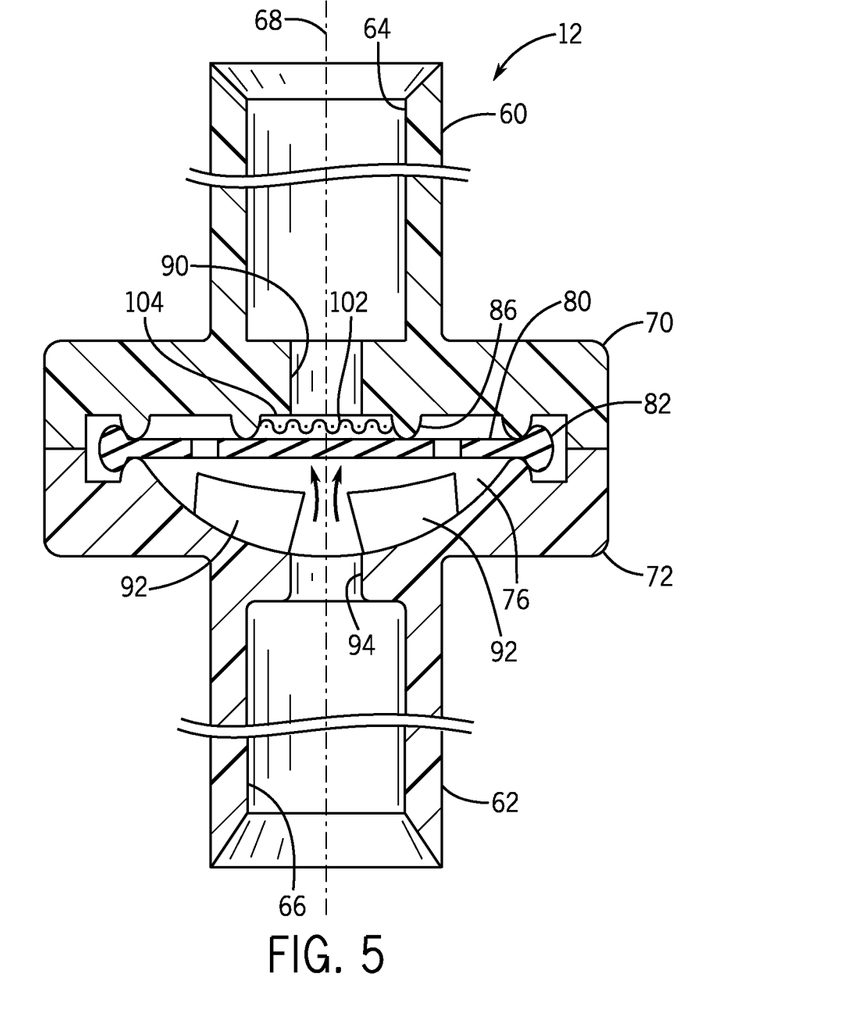
FIG. 5 is a figure similar to that of FIG. 3 showing a second embodiment of the invention.

Referring now to FIG. 5, in an alternative embodiment, the filter medium 102 may be attached to a lower face of the flanges 70 of the entrance housing section 60 facing the cavity 76 and within the annular valve seat 86. In particular, the downward opening 90 may open into a radially extending surface 104 within the valve seat 86 to which the periphery of the filter medium 102 is bonded using techniques as described above. In this location, upward back-flow of liquid against the elastomeric membrane 80 presses the center of the elastomeric membrane 80 into the filter medium 102 which supports the elastomeric membrane 80 preventing it from stretching beyond its elastic limit and suffering loss of function when subjected to very high back pressure. In all other respects, the valve 12 may be identical to that described above with respect to FIGS. 2 and 3.

This embodiment is particularly suited for punching the filter medium 102, for example, from a continuous sheet of filter media integrated into the injection molding process or by insert molding with disks die cut from a sheet of material and insert molding it at the time of molding of entrance housing section 60.

Figure 6:
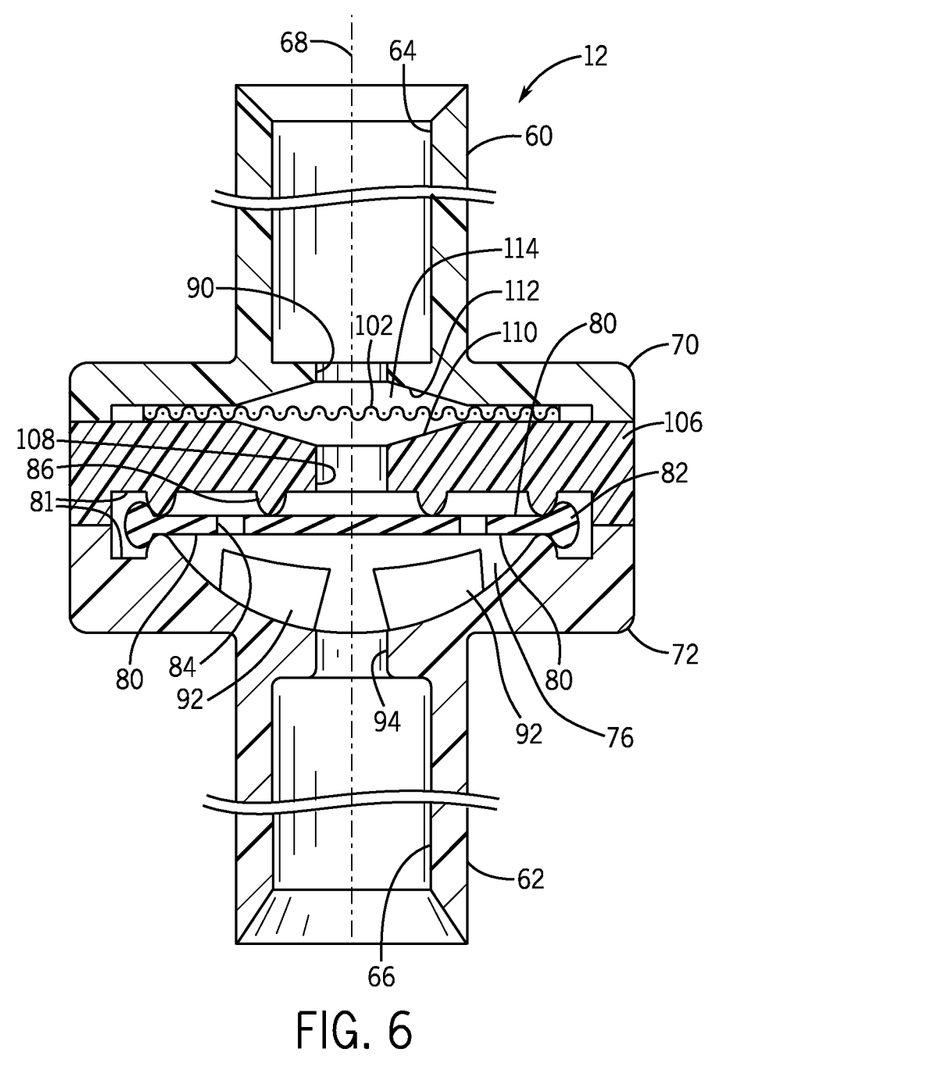
FIG. 6 is a figure similar to FIG. 5 showing a third embodiment of the invention.

Referring now to FIG. 6, in yet an alternative embodiment, flange 70 and 72 may be joined to each other by way of a valve seat component 106 having substantially equal diameter to flange 70 and 72 to join at its upper periphery to flange 70 (as depicted) and to join at its lower periphery to flange 72. Valve seat component 106 provides the annular valve seat 86 about a bore 108 axially aligned and corresponding generally in diameter to opening 90. The valve seat component 106 further provides a channel 81 to capture rim 82 of the elastomeric membrane 80 described above.

Importantly, the valve seat component 106 provides an upper countersink surface 110 around the upper edge of opening 89 mirroring and opposed to lower countersink surface 112 about the lower edge of opening 90. Filter medium 102 may be sandwiched between flange 70 and the upper surface of valve seat component 106 within a secondary cavity 114 formed by the opposed countersink surfaces 110 and 112 to extend across the axis 68 to filter flow between openings 90 and 89. This embodiment provides a greater filtration area by the effectively large diameter of the cavity 114.

As before, the filter medium 102 may be bonded to one or both of the flange 70 and valve seat component 106 by any of the means described above. Alternatively, the filter medium 102 may be simply mechanically clamped between these components. Cavity 114 allows increasing the filtration area without adversely affecting the size of the valve seat 86 or the channels 81 and hence the size of the elastomeric membrane 80. In all other respects, the valve 12 may be identical to that described above with respect to FIGS. 2 and 3.

Figure 7A:
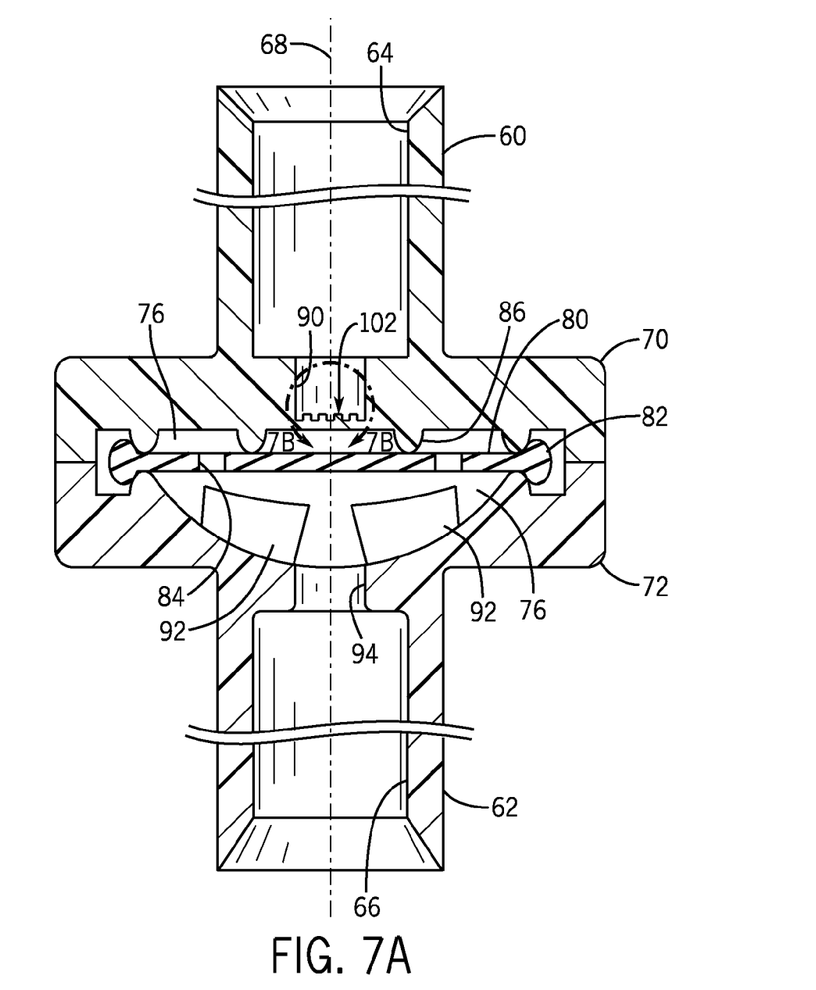
FIGS. 7a and 7b are figures similar to FIG. 6 showing a fourth embodiment of the invention with a molded filter and showing a fragmentary detail of that molded filter.
Figure 7B:
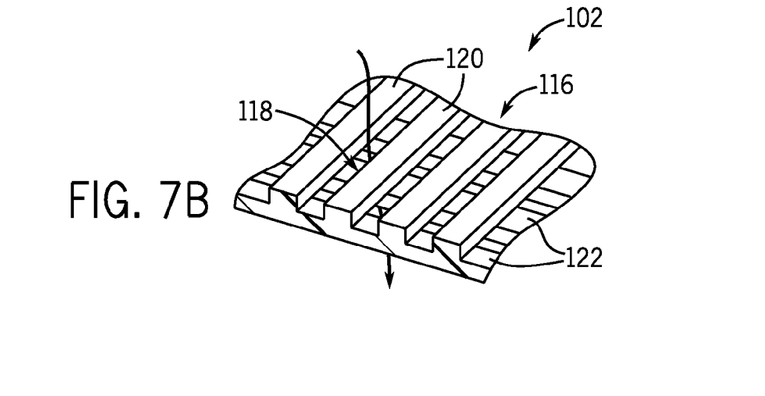

Referring now to FIGS. 7a and 7b, in yet an alternative embodiment, filter medium 102 may be formed by a molded grid 116 having a set of openings 118, for example, formed at spaces between crossing rectilinear elements 120 and 122 intersecting at right angles with elements 120 axially displaced with respect to rectilinear elements 122. The molded grid 116 may be integrally formed with entrance housing section 60 as part of the molding process of entrance housing section 60 so that the filter medium 102 is bonded to the entrance housing section 60 and extends across the lower edge of opening 90 to present a lower surface (as pictured) providing the supporting function of the elastomeric membrane 80 described above with respect to FIG. 5.

Figures 8A, 8B, 9:
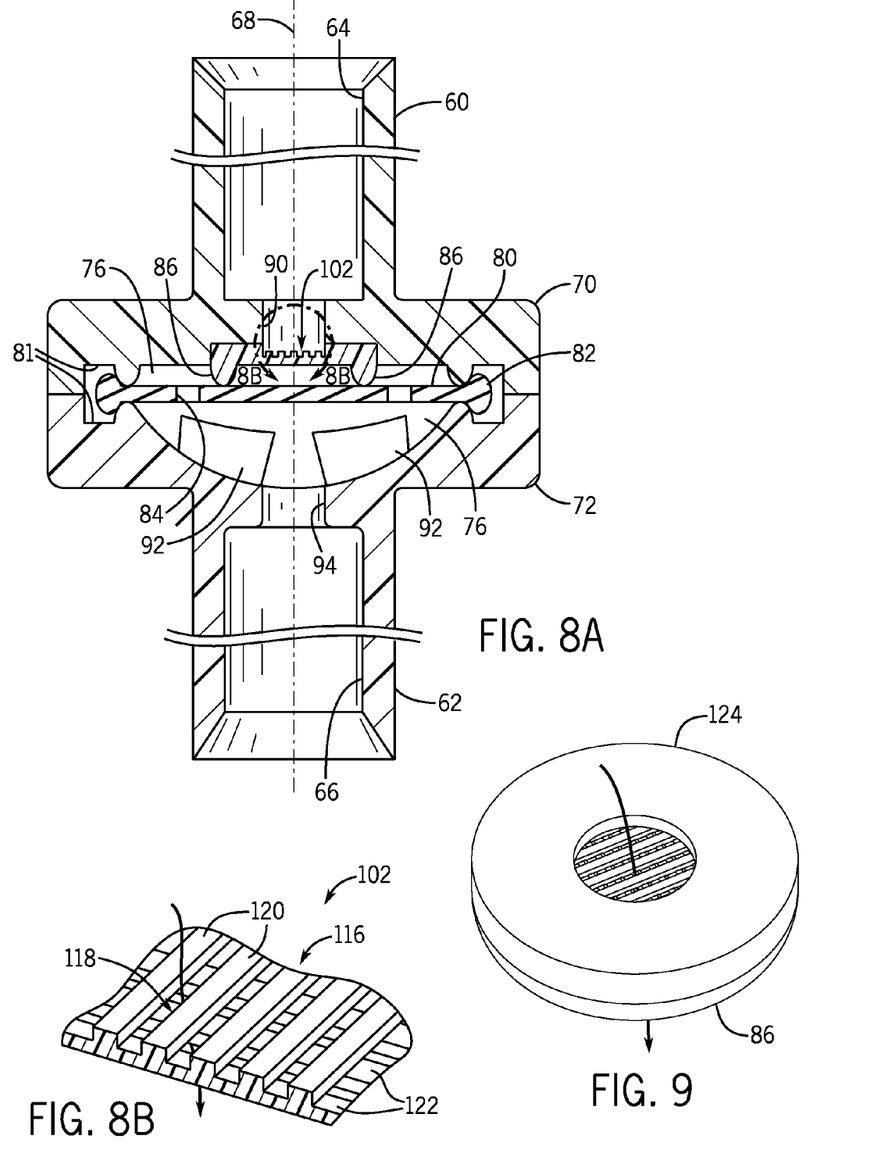
FIGS. 8a, 8b and 9 are figures similar to those of FIGS. 7a and 7b showing a fifth embodiment of the invention with a micro-molded filter.

Referring now to FIGS. 8a, 8b, and 9 in an alternative embodiment, the filter medium 102 may be molded as a separate component 124, for example, in the form of a disk incorporating on its lower surface the annular valve seat 86 and fitting within a cylindrical cavity of equal size at the lower edge of opening 90. By allowing this separate component 124 to be removable, it may be micro-molded to provide extremely small openings 118 in the grid 116 using a different molding process than used for the entrance housing section 60 and exit housing section 62. The filter medium 102, when installed, may again present a lower surface as depicted providing the supporting function of the elastomeric membrane 80 described above with respect to FIGS. 5 and 7. Filter medium 102 may be bonded or glued to the entrance housing section 60 or may be held by compression by the elastomeric membrane 80 at a point of contact with a rib 92.

Screen openings for filter medium 102 between 15 microns and 130 microns may be provided by various molding techniques.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

Various features of the invention are set forth in the following claims. It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

What is claimed is:

1. A combination check valve and filter comprising:
   a housing formed of first and second unitary molded thermoplastic elements joined to provide a cavity therebetween and providing fluid communication between an opposed entrance port formed in the first unitary molded thermoplastic element and an exit port formed in the second unitary molded thermoplastic element, wherein the entrance and exit ports are each adapted to connect sealably with an IV tube and the cavity is sealed except for openings through the entrance and exit port;
   a valve seat attached to a cavity wall formed by the first unitary molded thermoplastic element;
   a flexible diaphragm responsive to fluid flow through the cavity and positioned adjacent to the valve seat to seal against the valve seat with fluid flow from the exit port to the entrance port and to unseal away from the valve seat with fluid flow from the entrance port to the exit port; and
   a filter medium disposed in the housing between the entrance port and the valve seat;
   wherein the filter medium is integrally bonded at its periphery to the first unitary molded thermoplastic element; and
   wherein the entrance port provides a radial ledge with a surface facing away from the cavity and wherein the periphery of the filter medium abuts and is bonded to the surface.

2. The combination check valve and filter of claim 1 wherein the filter medium is selected from the group consisting of woven and nonwoven flexible fabrics.

3. The combination check valve and filter of claim 1 wherein the filter medium is bonded by embedding material of the filter medium within the thermoplastic of the first unitary molded thermoplastic element.

4. The combination check valve and filter of claim 1 wherein the valve seat is integrally molded with the first unitary thermoplastic element.

5. The combination check valve and filter of claim 1 wherein the entrance port and exit port are aligned along a central axis and first and second unitary molded thermoplastic elements provide flanges extending radially from the central axis about ends of the entrance port and exit port, the flanges joined at their peripheries to create the cavity.

6. The combination cheek valve and filter of claim 5 wherein the flanges provide axially extending features that capture a periphery of the flexible diaphragm therebetween so that an entire periphery of the flexible diaphragm is held substantially stationary when the flexible diaphragm seals against the valve seat and unseals away from the valve seat.

7. A combination check valve and filter comprising:
   a housing formed of first and second unitary molded thermoplastic elements joined to provide a cavity therebetween and providing fluid communication between an opposed entrance port formed in the first unitary molded thermoplastic element and an exit port formed in the second unitary molded thermoplastic element wherein the entrance and exit ports are each adapted to connect sealable with an IV tube and the cavity is sealed except for openings through the entrance and exit port;
   a valve seat attached to a cavity wall formed by the first unitary molded thermoplastic element;
   a flexible diaphragm responsive to fluid flow through the cavity and positioned adjacent to the valve seat to seal against the valve seat with fluid flow from the exit port to the entrance port and to unseal away from the valve seat with fluid flow from the entrance port to the exit port; and a filter medium disposed in the housing between the entrance port and the valve seat;

wherein the filter medium is integrally bonded at its periphery to the first unitary molded thermoplastic element wherein the valve seat extends about an opening of the entrance port into the cavity and wherein the periphery of the filter medium covers the opening and is bonded to a cavity wall within the valve seat; and wherein the filter medium abuts the flexible diaphragm when the flexible diaphragm seals against the valve seat to support the flexible diaphragm.

8. The combination check valve and filter of claim 7 wherein the filter medium is selected from the group consisting of woven and nonwoven flexible fabrics.

9. The combination check valve and filter of claim 7 wherein the filter medium is bonded by embedding material of the filter within the thermoplastic of the first unitary molded thermoplastic element.

10. The combination check valve and filter of claim 7 wherein the valve seat extends about an opening of the entrance port into the cavity and wherein the filter medium covers the opening and the filter medium is a perforated thermoplastic element, integrally molded as part of the first unitary molded thermoplastic element.

11. The combination check valve and filter of claim 10 wherein the perforated thermoplastic element provides a grid of a set of crossing rectilinear elements, the elements of each set crossing to abut at regular intersections.

12. A combination check valve and filter comprising:

a housing formed of separately molded first and second unitary molded thermoplastic elements joined to provide a cavity therebetween and providing fluid communication between an opposed entrance port formed in the first unitary molded thermoplastic element and an exit port formed in the second unitary molded thermoplastic element wherein the entrance and exit ports are each adapted to connect sealably with an IV tube and the cavity is sealed except for openings through the entrance and exit port;

a valve seat;

a flexible diaphragm responsive to fluid flow through the cavity and positioned adjacent to the valve seat to seal against the valve seat with fluid flow from the exit port to the entrance port and to unseal away from the valve seat with fluid flow from the entrance port to the exit port; and a filter medium disposed in the housing between the entrance port and the valve seat;

wherein the valve seat is a third unitary molded thermoplastic element, separately molded from the first and second unitary molded thermoplastic elements and positioned between the first and second unitary molded thermoplastic elements retained thereby when the first and second unitary molded thermoplastic elements;

wherein the third unitary molded thermoplastic element provides a central aperture having a first opening surrounded by the valve scat on a first side of the third unitary molded thermoplastic element facing the cavity and having a second opening on a second opposite side of the third unitary molded thermoplastic element:, and wherein the periphery of the filter medium abuts and is bonded to the second opposite side of the third unitary molded thermoplastic element about the second opening.

13. The combination check valve and filter of claim 12 wherein the filter medium covers the central aperture and the filter medium is a perforated thermoplastic element integrally molded as part of the third unitary molded thermoplastic element.

* * * * *